(12) United States Patent
Burks et al.

(10) Patent No.: US 10,598,635 B2
(45) Date of Patent: Mar. 24, 2020

(54) SYSTEMS AND METHODS OF CAPTURING TRANSIENT ELASTIC VIBRATIONS IN BODIES USING ARRAYS OF TRANSDUCERS FOR INCREASED SIGNAL TO NOISE RATIO AND SOURCE DIRECTIONALITY

(71) Applicant: Digital Wave Corporation, Centennial, CO (US)

(72) Inventors: Brian M. Burks, Centennial, CO (US); Steven M. Ziola, Centennial, CO (US)

(73) Assignee: HEXAGON TECHNOLOGY AS, Alesund (NO)

( * ) Notice: Subject to any disclaimer, the term of this patent is extended or adjusted under 35 U.S.C. 154(b) by 0 days.

(21) Appl. No.: 15/797,596

(22) Filed: Oct. 30, 2017

(65) Prior Publication Data
US 2018/0284073 A1    Oct. 4, 2018

Related U.S. Application Data

(60) Provisional application No. 62/480,193, filed on Mar. 31, 2017.

(51) Int. Cl.
*G01N 29/44*    (2006.01)
*G01N 29/38*    (2006.01)
(Continued)

(52) U.S. Cl.
CPC ......... *G01N 29/4427* (2013.01); *G01N 29/14* (2013.01); *G01N 29/28* (2013.01);
(Continued)

(58) Field of Classification Search
CPC . G01N 29/4427; G01N 9/38; G01N 2291/106
(Continued)

(56) References Cited

U.S. PATENT DOCUMENTS

| 4,671,379 A | * | 6/1987 | Kennedy | G01V 1/005 166/177.2 |
| 5,594,706 A | * | 1/1997 | Shenoy | G01V 1/48 367/25 |

(Continued)

OTHER PUBLICATIONS

Increasing Sensor Spacing in Modal Acoustic Emission Testing via Increased Sensor Sensitivity and Phased Array Modal Acoustic Emission (PA-MAE), Brian M. Burks, Digital Wave Corporation, Draft Mar. 2016.

(Continued)

*Primary Examiner* — Natalie Huls
*Assistant Examiner* — Monica S Young
(74) *Attorney, Agent, or Firm* — Furman IP Law

(57) ABSTRACT

Provided herein are systems and methods for real time processing of signals from an array of transducers for detecting transient elastic waves originating from unknown locations in a body, which may propagate in a dispersive fashion. The systems and methods allow real time combination and analysis of signals, including decisions regarding storage as new data is received. The methods described herein include designing arrays of detectors and methods for processing signals in real time given the constraints of the body under test determining whether to store the set of information while a new set of information is received for processing within a real time environment. The methods described herein include methods which result in the determination or small time shifts which place all signals into a coherent time base which are then combined achieving a composite waveform that possesses an increased signal-to-noise ratio over any single element.

6 Claims, 11 Drawing Sheets

(51) Int. Cl.
*G01N 29/50* (2006.01)
*G01N 29/28* (2006.01)
*G01N 29/14* (2006.01)

(52) U.S. Cl.
CPC ......... *G01N 29/38* (2013.01); *G01N 29/4436* (2013.01); *G01N 29/50* (2013.01); *G01N 2291/0231* (2013.01); *G01N 2291/106* (2013.01)

(58) Field of Classification Search
USPC ............................................................ 73/597
See application file for complete search history.

(56) References Cited

U.S. PATENT DOCUMENTS

| | | | |
|---|---|---|---|
| 6,202,489 B1 | 3/2001 | Beffy | |
| 2002/0130591 A1 | 9/2002 | Fraser | |
| 2004/0245315 A1* | 12/2004 | Maev | G01N 29/262 228/8 |
| 2006/0039238 A1* | 2/2006 | Mandal | G01V 1/48 367/31 |
| 2008/0110266 A1 | 5/2008 | Randall | |
| 2009/0048789 A1* | 2/2009 | Yu | G01N 29/069 702/39 |
| 2009/0067286 A1* | 3/2009 | Bose | G01V 1/48 367/38 |
| 2009/0241675 A1 | 10/2009 | Takada | |
| 2010/0101326 A1 | 4/2010 | Iizuka | |
| 2013/0114376 A1* | 5/2013 | Aeron | G01V 1/30 367/32 |
| 2016/0209538 A1* | 7/2016 | Wang | G01V 1/48 |
| 2017/0205388 A1* | 7/2017 | Thomas | G01N 33/383 |

OTHER PUBLICATIONS

International Search Report (ISR) and Written Opinion of the International Searching Authority (ISA) for PCT Application No. PCT/US2018/025603, dated Jun. 14, 2018 by USPTO to International Bureau.

* cited by examiner

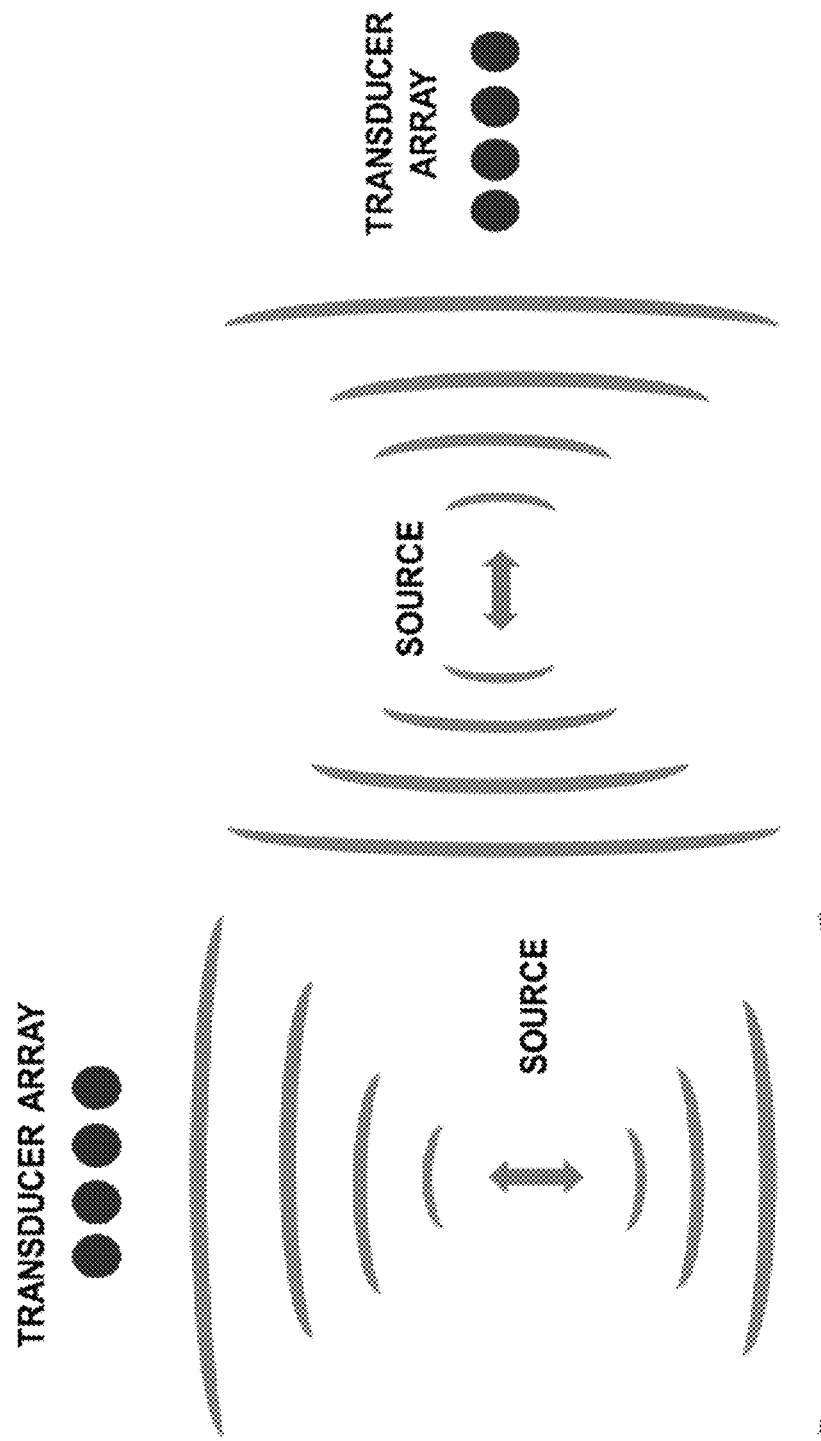

| Angle of Propagation [deg] | Element 1-2 dt [µs] | Element 3-2 dt [µs] | Element 4-2 dt [µs] |
| --- | --- | --- | --- |
| 0 | -20.8 | -1.2 | 39.2 |
| 15 | -18.2 | 19.4 | 39.2 |
| 30 | -18.6 | 19.6 | 35 |
| 45 | -16 | -4.8 | 32.4 |
| 60 | -9.6 | 12.8 | 19.2 |
| 75 | -4.4 | 4.0 | 4.4 |
| 90 | -0.8 | 0.2 | -1 |

Fig. 9

| Angle of propagation [deg] | Single channel PP signal [dB] | Analog Summation PP Signal [dB] | Analog summation sensitivity increase [dB] | Digitally shifted and summed Signal [dB] | PA-MAE sensitivity increase [dB] |
|---|---|---|---|---|---|
| 0 | 53.8 | 56.0 | 2.2 | 60.7 | 6.9 |
| 15 | 55.8 | 55.9 | 0.1 | 66.4 | 10.6 |
| 30 | 58.4 | 58.1 | -0.3 | 69.6 | 11.2 |
| 45 | 47.3 | 49.7 | 2.4 | 55.5 | 8.2 |
| 60 | 50.4 | 50.3 | -0.1 | 60.3 | 9.9 |
| 75 | 50.5 | 58.9 | 8.4 | 60.5 | 10.0 |
| 90 | 54.9 | 63.7 | 8.8 | 64.7 | 9.8 |

Fig. 10

SYSTEMS AND METHODS OF CAPTURING TRANSIENT ELASTIC VIBRATIONS IN BODIES USING ARRAYS OF TRANSDUCERS FOR INCREASED SIGNAL TO NOISE RATIO AND SOURCE DIRECTIONALITY

PRIORITY STATEMENT

This application claims the priority of provisional application No. 62/480,193, filed Mar. 31, 2017 and entitled "Methods and Systems for Sensor Spacing in Modal Acoustic Emission Testing," the contents of which are fully incorporated herein for all purposes.

FIELD OF THE TECHNOLOGY

The present disclosure relates to detecting transient elastic waves in bodies with arrays of transducers, detectors, transceivers, or receivers.

SUMMARY OF THE DESCRIPTION

Provided herein are systems and methods for real time processing of signals from an array of transducers for detecting transient elastic waves originating from unknown locations in a body, which may propagate in a dispersive fashion. The systems and methods allow real time combination and analysis of signals, including decisions regarding storage as new data is received. The methods described herein provide for designing the array of detectors and methods for processing the signals in real time given the constraints of the body under test determining whether to store the set of information while a new set of information is received for processing within a real time environment ensuring an increase in sensitivity of the system. The methods described herein include methods which result in the determination or small time shifts which place all signals into a coherent time base which are then combined achieving a composite waveform that possesses an increased signal-to-noise ratio over any single element.

In one aspect, the disclosure describes a method including determining in real time whether to store in a computer memory a first set of samples from a plurality of signals from a multi-element transducer array that is coupled to a body of material under test within a real time processing environment. The first set of samples represents a first time range and ends with a first boundary set of samples that are later also processed along with a second set of samples representing the plurality of signals for a second time range possessing a necessary overlap at the end of the first time range, thereby creating an overlapping plurality of processed samples including samples that are processed with the first set of samples and processed with the second set of samples. The overlapping plurality of processed samples is sufficient to capture in the multi-element transducer array a slowest-measured wave of interest in the body under test. The slowest-measured wave of interest is both sensed by a first portion of the multi-element transducer array during the first time range and sensed by a second portion of the multi-element transducer array during the second time range. The determining in real time whether to store the first set of samples further comprises calculating a plurality of respective delay times for each of the plurality of signals with respect to a predetermined reference signal of the plurality of signals, such that a time-shift by the plurality of respective delay times modifies the plurality of signals into a time-base-coherence with the predetermined reference signal. The determining in real time further comprises combining at least one of the time-shifted plurality of signals with the reference signal of the plurality of signals, thereby creating a real time combined signal from the plurality of signals. The determining in real time further comprises evaluating the real time combined signal over the first set of samples for values of the real time combined signal that exceed a predetermined threshold. The determining in real time further comprises indicating an instruction to store the first set of samples in the computer memory if, within the first set of samples, the real time combined signal crosses a predetermined threshold in the real time combined signal.

In another aspect, the disclosure further describes a system including a body of material under test that is adapted to detect propagating transient elastic vibrations possessing a slowest moving wave component as transmitted through the body of material from a source of that transient elastic wave deformation information to the multi-element transducer array. The system further includes a maximum pitch of the multi-element transducer array coupled to the body pre-determined by computational and memory limits of the hardware and its ability to determine coherency of the signals from the multi-element transducer while maintaining the required positive overlap so as to ensure increased sensitivity. The system further includes a receiver circuit for processing a plurality of signals received from multi-element transducer array. The receiver circuit further comprises a circuit for determining a time delay between a first reference signal of the plurality of signals and the other signal(s). The receiver circuit further comprises a combination circuit for creating a combined signal based on the time shifted signals. The receiver circuit further comprises a threshold-detecting circuit for detecting in real time values of an output of the combination circuit above a threshold at times when none of the plurality of the received signals may have a value over the threshold.

Other embodiments and features of the present disclosure will be apparent from the accompanying drawings and from the detailed description which follows.

BRIEF DESCRIPTION OF THE DRAWINGS

FIG. 4 show the effects of source orientation of a vibration source with respect to a transducer array.

FIG. 5 shows additional effects of source orientation of a vibration source with respect to a transducer array.

FIG. 9 shows timing differential calculated for various angles of incidence for summation of signals in an exemplary linear array of four elements.

FIG. 10 shows increases in flexure mode amplitude for alternative summation possibilities for a body under test as compared to the methods described for digital real time summation herein.

The embodiments are illustrated by way of example and not limitation in the Figures of the accompanying drawings in which like references indicate similar elements.

DETAILED DESCRIPTION

The following patent description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one. Reference in this specification to "one embodiment" or "an embodiment" or the like means that a particular feature, structure, or characteristic described in connection with the embodiment is included in at least one embodiment of the disclosure. The appearances of the phrase "in one embodiment" or the like in various places in the specification are not necessarily all referring to the same embodiment, nor are separate or alternative embodiments mutually exclusive of other embodiments. Moreover, various features are described that may be exhibited by some embodiments and not by others.

Figure 1:
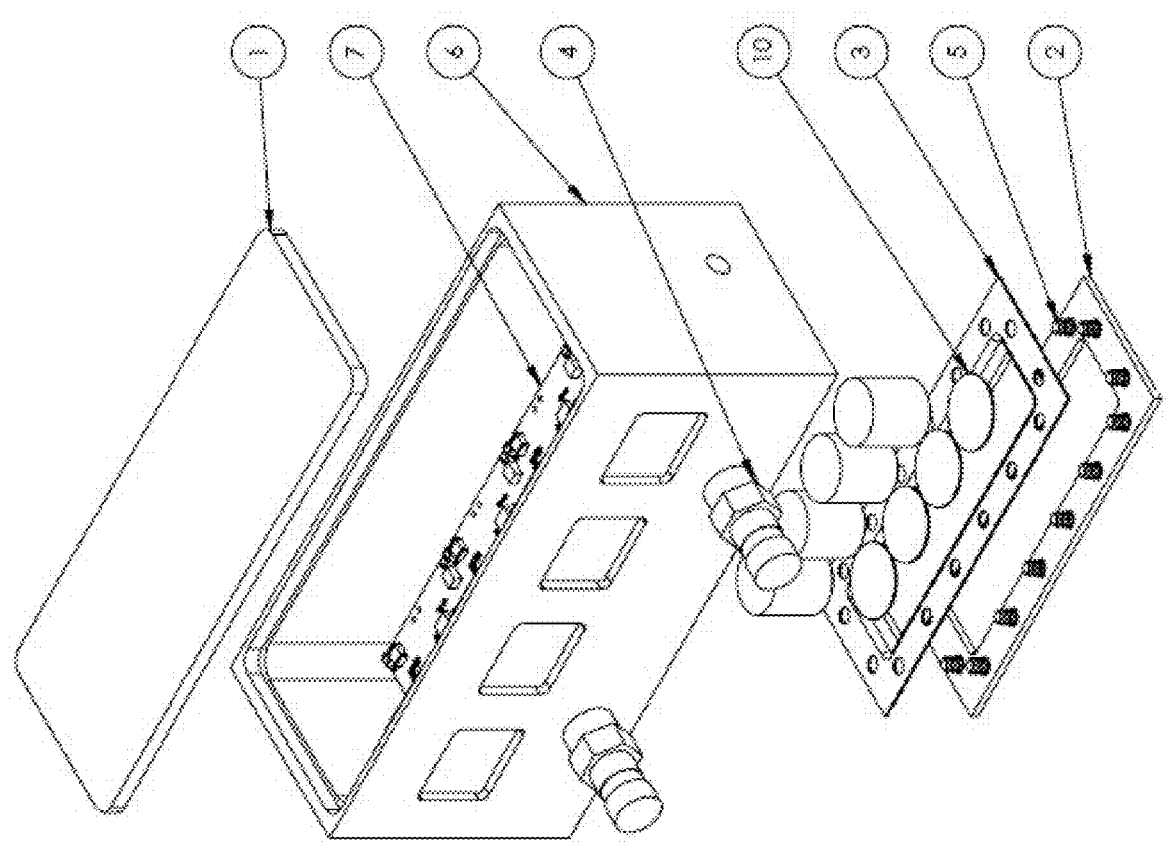
FIG. 1 shows an exploded view of an exemplary transducer array as described herein, including associated electronics and channels for each of the transducer elements.

FIG. 1 shows an exemplary transducer array as described further herein with four transducer elements and four separate data channels for transmitting data for processing and/or storage. The transducer array is arranged between interface portions 10 and an array housing 6, which may have a removable lid 1 and may be pressurized via ports 4. The housing 6 contains electronics, such as shown on circuit board 7. Interface portions 10 may be covered or arranged by an optional barrier 3 (e.g., a water tight barrier) that is held by frame 2 and fasteners 5 intended to create a compliant fluid filled bladder. In certain measurement scenarios, (e.g., when needing to couple to a rough or highly irregular surface, or when automating sensor placement) it is not possible to couple traditional sensors with a stiff interface between the part under test and the piezoelectric element; in these scenarios, the compliant fluid filled bladder enables coupling to the part under test. By filling the compliant bladder with a fluid (where only dilatational wave propagation is supported) the fidelity of the measured waveforms may be acceptably preserved with adequate coupling.

The array housing 6 shows an equal number of ports for relaying data from the circuit board 7 for further processing. In another embodiment several or all of the channels of data may also be multiplexed together onto a single port or channel for the purpose of transmission.

However, regardless of how the signals and data are transmitted from transducer through the electronics, to complete the real time processing described herein, the samples of data received must be processed by the methods without loss of data. As described further herein, operating these methods in real time and without a loss of data requires an overlap of sample processing and effectively an overlap of samples in the system.

Figure 2:
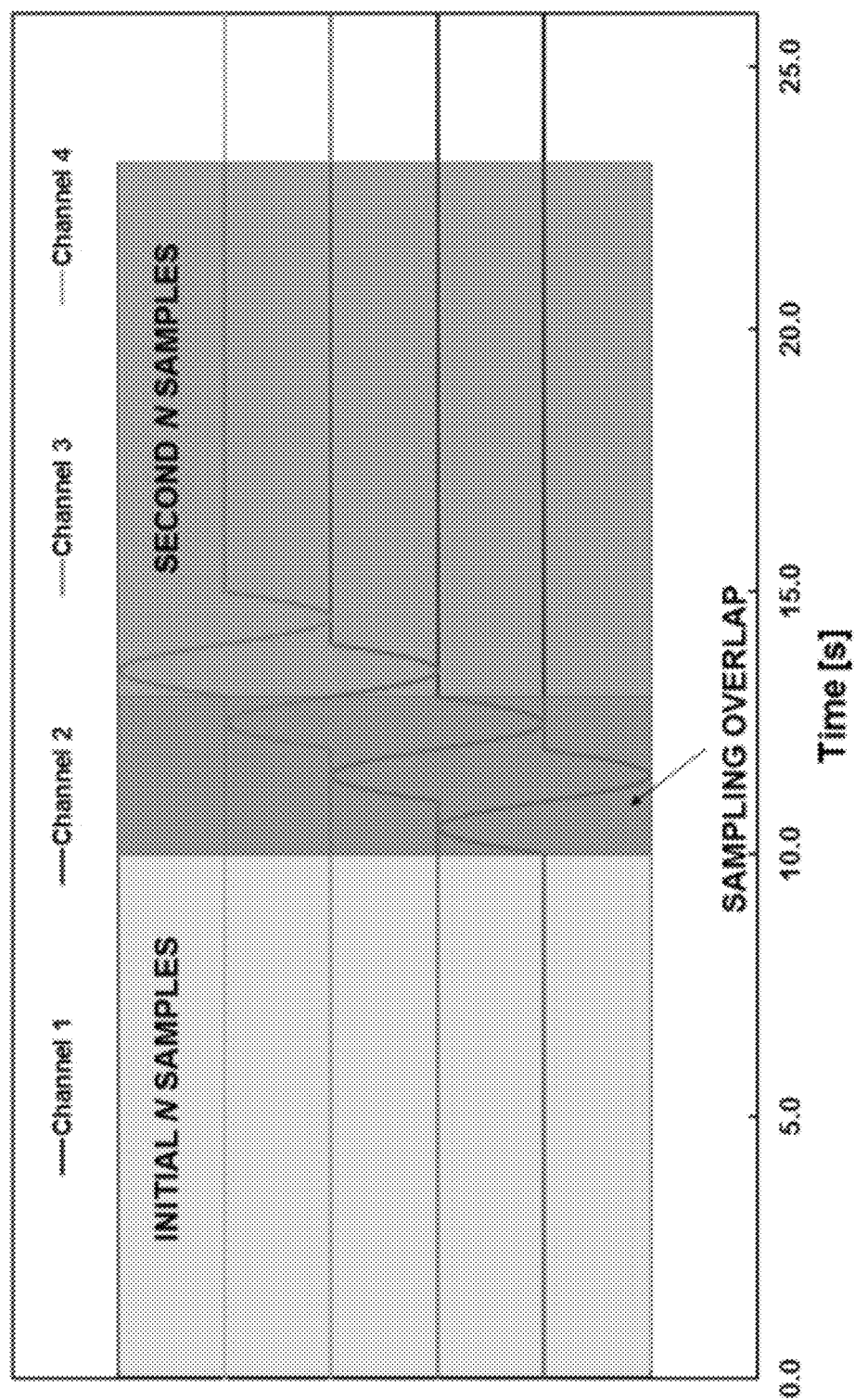
FIG. 2 shows an exemplary graph describing an overlap of samples for use in determining in real time whether to store a first set of samples.

FIG. 2 shows an exemplary graph describing an overlap of samples for use in determining in real time whether to store a first set of samples. The disclosed methods utilize arrays of particular configurations to process in real time signals from the arrays in manners that increase signal to noise ratios (SNR) for the received signals beyond those of any of the single channels. The graph shows the positive sample overlap that is required to detect events by an array without the possibility of missing an event that could cross the thresholds described and claimed herein, thus ensuring real time performance and collection of data.

A single exemplary event is illustrated as it would be detected by each of the transducers of the array, and the single event is captured by the sufficient positive sample overlap. This positive sample overlap illustrates the outcome of a set of engineering decisions for implementing the systems and methods described herein. The illustrated wave in the single exemplary event represents the slowest-moving wave component in the frequency band of interest for the body under test determined from the dispersion relations (or bulk wave propagation velocities, as appropriate), wave modes of interest, and transducer array geometry. Each of these aspects of this real time determination will be defined in various embodiments further herein.

The disclosed methods allow for determinations to be made in real time based on the materials under test, and the specific transducer array characteristics and geometries. These decisions must be made with sufficient information about events that might be missed due to the event arriving to parts of the array in one set of samples and arriving in other parts of the array in another set of samples. For example, a real time decision may be made within the real time environment described herein about storing, transmitting, and/or further processing for each set of N samples such that data and/or events are not lost or missed by these decision-making processes. These decisions allow for an advanced real time triggering decision that facilitates an increase in the signal to noise ratio (SNR) of the array as compared to the SNR for individual elements of the transducer array. These decisions include processes for detecting a set of time differences for coherently combining the data, combining the data into a composite signal, and analyzing the signal before making a decision on storing the information and beginning processing on the next set of data received.

The overlap of samples shown in the figure represents an amount of time in which the samples may be processed by the analysis processes herein (e.g., including decisions made regarding storage) on a first set of samples while a second set of samples are received. The overlap in time of the first set of samples and the second set of samples ensures that for a given sample rate, the slowest moving wave component must be detected in the same set of samples so as to enforce the increase in SNR of the array.

Therefore, the boundary set of samples is processed with both the first set of samples and the second set of samples. As used herein, the terms boundary set of samples and sample overlap may be used interchangeably to describe this set of samples that is processed with both the first set of samples and the second set of samples, with no gap of samples being processed by the method in real time. The real time processing requirement may be expressed as a positive overlap in processing time, specifically for a positive overlap that there is more processing time available than processing time required to process (e.g., analyze, combine, store) a set of samples, including related boundary sample sets, while another set of samples is received for processing.

Timing requirements for real time processing requires a positive sample overlap as shown in the figure. This positive overlap creates the ability to capture an exemplary event within the array and process the entirety of the event within the time represented by one set of samples. In this way, the array of transducers may properly capture the transient elastic waves in the body under test coming from an event located at any angle relative to the array. The largest overlap required for real time processing occurs events registering the largest timing differential between the events arriving at each of the transducers, as measured by the slowest moving wave of the transient elastic waves coming from the event within a frequency band of interest. Therefore, the positive sample overlap, or the processing time overlap, that is required for real time processing may be calculated from the separation of the transducers receiving the transient elastic waves in the body under test, sample rate, and the speed of the slowest moving wave of an expected event to be detected.

As described further herein, the combination of signals by the methods herein requires that at least two signals (and often more, such as four, nine, sixteen, etc. signals) detected from the event must be combined in order to maintain the described gains in the effective signal to noise ratios of the transducers. These gains may be necessary to detect certain events above the noise level or to increase the spacing of sensors while still maintaining adequate coverage of the structure, as described further herein. Therefore, the methods described herein may include systems with specific characteristics that are used to ensure real time processing may be achieved without losing data.

For example, as shown in FIG. 2, an initial N samples representing 13 seconds of monitored time (t=0-13 seconds) has designated as a boundary set of samples as its final 3 seconds of time (from 10-13 seconds) before a second set of N samples begins (e.g., at 13 seconds on the graph). Thus, in the exemplary embodiment shown in the figure, in order to process the initial N samples in real time, the samples representing from 0 seconds to 13 seconds must be stored in physical memory and their time coherency determined while the second N samples are received for their own processing (digitization, physical memory storage, and time coherency determination). To ensure the real time increases by the array in the SNR of the combined signal, the computational power of the hardware must be such that the time coherency of the sets of N samples and their respective boundary sets is determined, and a triggering decision made (either passing data on to a PC for storage if the threshold was exceeded, or clearing the physical memory space if a trigger did not occur) prior to the available memory overflowing.

Shown in the figure are a boundary set of samples representing times representing 10 seconds to 13 seconds. This boundary set of samples is processed both with the initial set of N samples as well as being processed with the second set of N samples representing times from 13 seconds to 23 seconds. This process is thereafter repeated, for example with samples from 20-23 seconds forming a second boundary set of samples between the second set of N samples and a third set of N samples representing data from 23-33 seconds. This second boundary set of samples would be processed both with the second set of N samples as well as the third set of N samples.

In this manner, as shown in FIG. 2, despite the event arriving on the top channel after 13 seconds and after the first N samples (and first boundary set of samples) have completed, the event may still be captured by the analysis of the second set of N samples that also includes the first set of boundary samples. In some instances, the event would be missed by the analysis of the first set of N samples and boundary samples alone. For example, in some instances the event may be missed if the first N samples and boundary samples did not contain enough of the event such that summation of the signals as described herein did not bring the combined signal over threshold.

As another example, consider transient elastic vibrations propagating in a plate-type structure having calculated dispersion relations. Further, consider a source with dominant out-of-plane source orientation that preferentially excites the flexure mode. From the dispersion relations of the plate/material property combination, it is determined that the slowest moving component of the flexure mode for the lowest frequency of interest in the test is 0.8 mm/µs. The final information necessary to determine the necessary time overlap is the array geometry and inter-element pitch. For this example, consider a four (4) element 1D array with inter-element pitch of 15.9 mm. From this information, it is determined that in the limiting case (parallel source orientation relative to a 1D array) the maximum distance for the wave to traverse through the array will be from element four and element one (or vice versa). From the velocity of the slowest moving wave component (0.8 mm/µs), it is determined that a minimum time overlap of 59.625 µs is required to ensure no gap in data acquisition to enforce the real time increase in SNR of the array.

The timing and sample sizes discussed herein for this figure are exemplary and may be markedly different in various applications based on the specifics of arrays of transducers monitoring bodies under test, wave velocities, and frequencies of interest. For example, while certain arrangement and processing constraints may be illustrated by an inter-element pitch of 15.9 mm or by a sample overlap representing a boundary time frame of 3 seconds, other applications may have different pitches or much shorter boundary times, as calculated as described herein based on transducer dimensions and/or characteristics of the measured elastic waves.

Specific discussions for choosing the sampling frequency for embodiments are not included in this disclosure because the techniques are well discussed in digital signal processing works. In general, sampling rates must be sufficient such that the highest frequency component of interest satisfies the Nyquist frequency criterion and is not eliminated by an anti-aliasing filter.

Figure 3A:
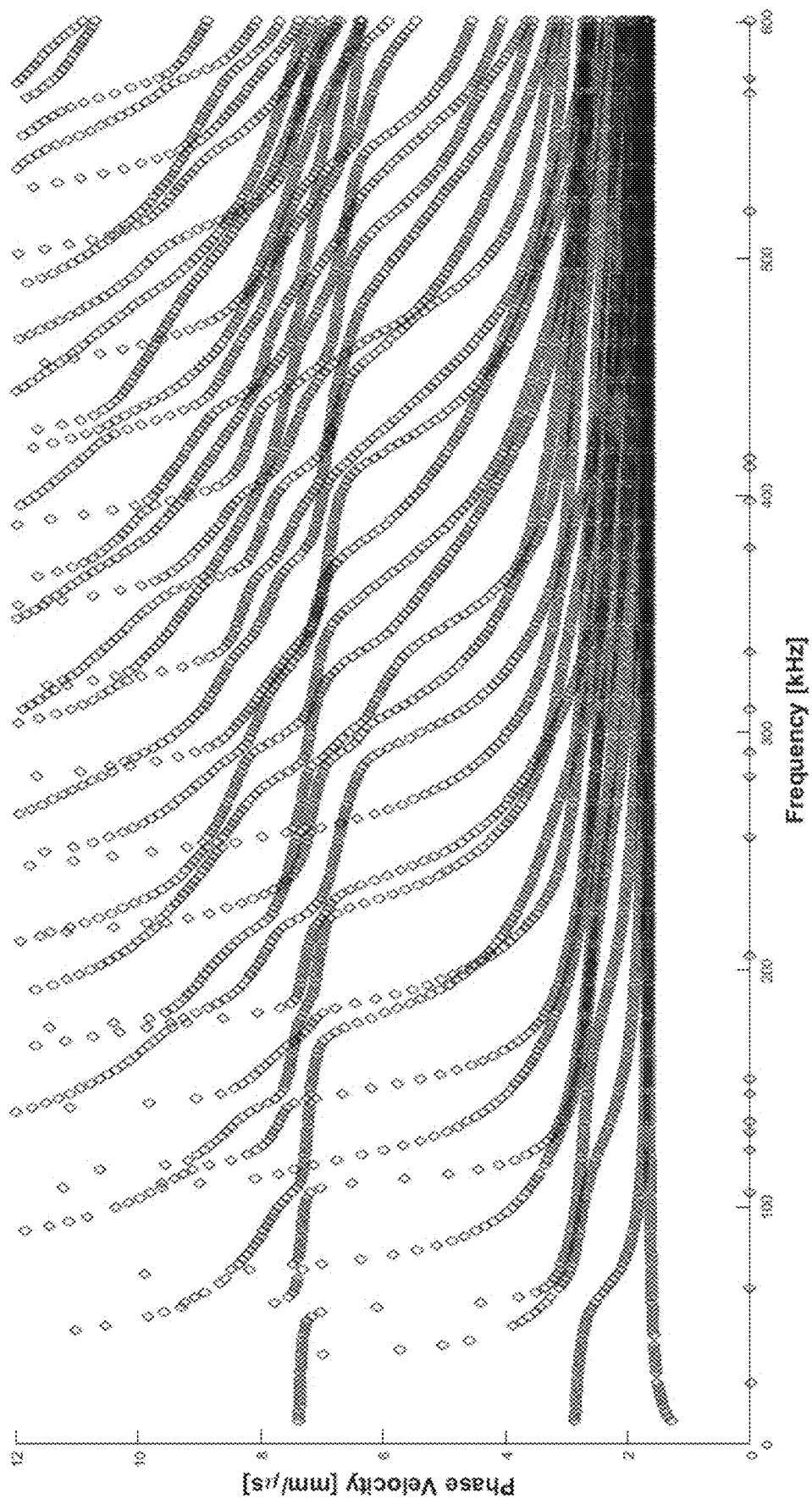
FIGS. 3A-3C illustrate the angular dependence on phase velocity of transient elastic vibrations during transmission along a hoop direction, an axial direction and 45 degrees to the axial direction of an exemplary test composite vessel.
Figure 3B:
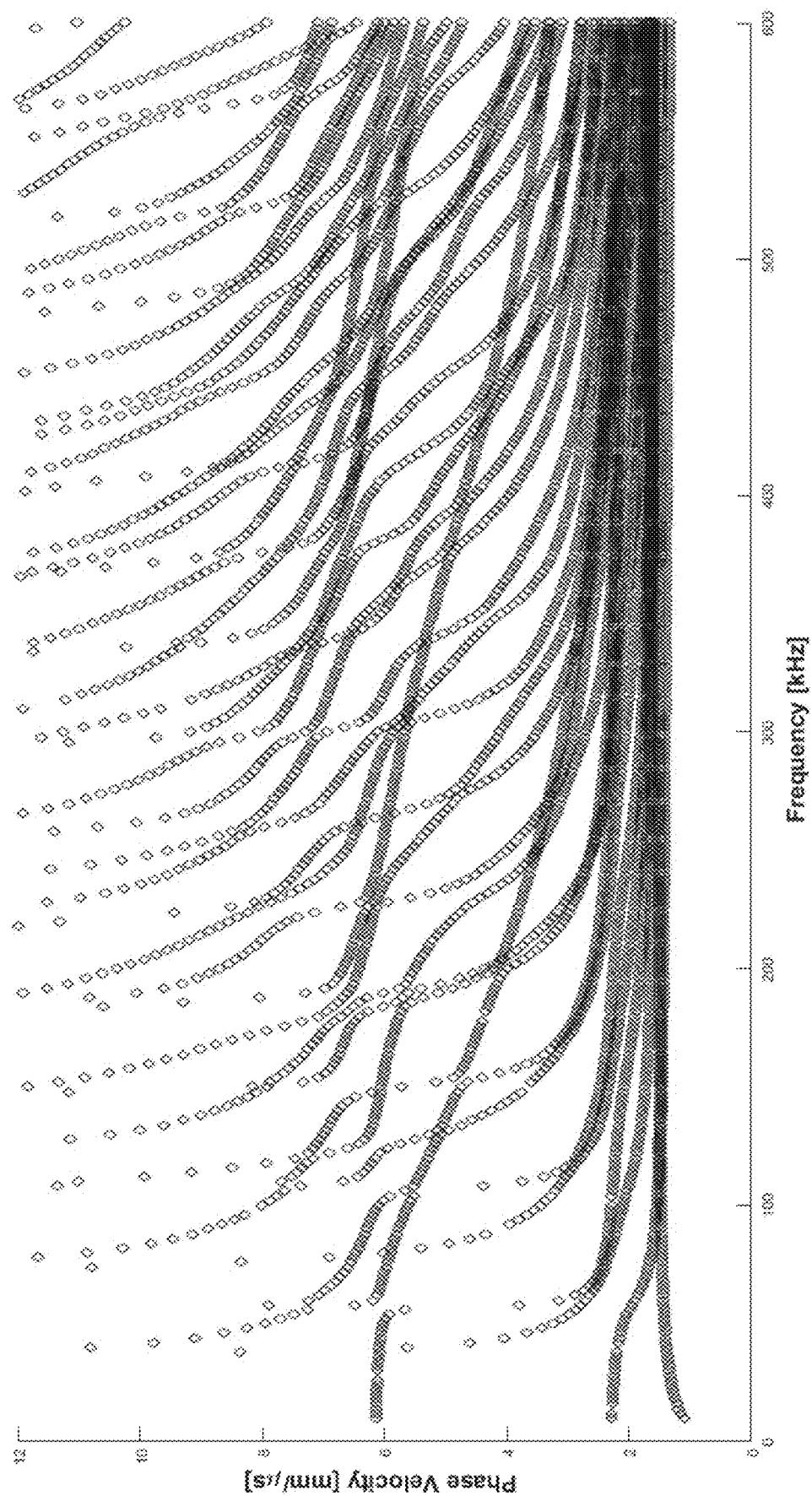
Figure 3C:
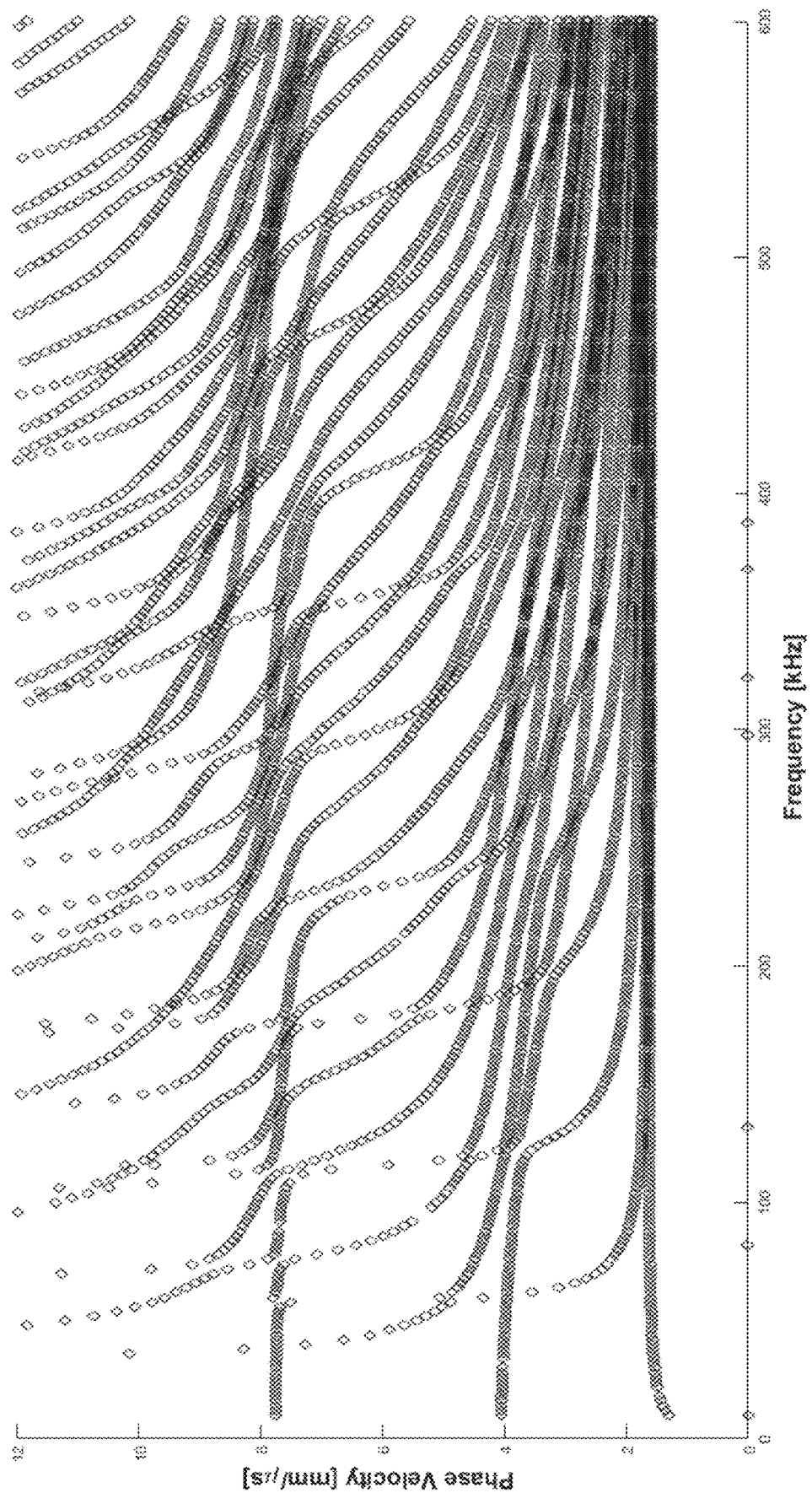

FIGS. 3A-3C illustrate the angular dependence on phase velocity of transient elastic vibrations during transmission along a hoop direction, an axial direction and 45 degrees to the axial direction of an exemplary test composite vessel. FIG. 3A shows a set of dispersion relations of elastic waves travelling along a hoop direction of the composite pressure vessel. FIG. 3B shows a set of dispersion relations of elastic waves travelling along an axial direction of the composite vessel. FIG. 3C shows a set of dispersion relations of elastic waves travelling at 45 degrees to the axial and hoop directions of the composite pressure vessel. Other bodies under test may have different bulk ultrasonic or bulk seismic wave velocities and arrays of transducers may use these different wave velocities as described further herein to determine proper array geometries and numbers of transducers as well as to determine a location of an event. From FIGS. 3A-3C, it is clear that mode velocity can be highly dependent upon propagation direction of that mode in the body under test. A dispersion relation may include different wave modes (e.g., extensional wave modes, flexural wave modes) of the elastic waves through the body under test. These various characteristics of the transient elastic waves may be used to design the transducer array and to modify the methods herein (e.g., maximum number of lags to consider in a time shifting algorithm, or number of computations necessary for time coherency determination) for real-time analysis and storage decision making.

Techniques in active phased array ultrasonic testing (PAUT) may use inverse time delays that are imposed on the detected signals for each element according to the focal law in order to time shift all detected waveforms into a zero time register and the resulting time-shifted coherent waveforms are then summed to produce a composite Amplitude Scan (or A-Scan). Conventional phased array sensing provides for a considerable level of increase in the sensitivity (and SNR) of received signals for PAUT. Utilization of the increase in detection sensitivity from the summation of signals from the phased array in PAUT, where bulk ultrasonic waves propagate from a known focal point, is a straightforward endeavor as the ultrasonic waves are non-dispersive (i.e., velocity is constant for all frequencies), and the focal law may be utilized to set the appropriate time shifts for each element so as to shift each elements waveform back into a zero register. In passive waveform measurement situations (e.g., Modal Acoustic Emission (MAE) testing, seismology, etc.) where sources are broadband, wave propagation can be both dispersive, and sources originate at unknown locations relative to the array a closed form set of time delays is not applicable in time shifting the waveforms from multiple elements into coherence. However, using the methods described herein to analyze the signals in real time, SNR gains analogous to those achieved in PAUT applications may be achieved for transient elastic waves measured in situations where closed form time reversal laws are not applicable (i.e., broadband sources, dispersive wave propagation, and/or unknown source origination).

The tested composite pressure vessels allow for precise geometry and configuration measurements to be made in order to establish the real time ability of the methods described herein for processing in real time. These tests on composite pressure vessels confirmed that the methods correctly determined the proper timing differentials in real time despite the dispersive, multi-mode, attenuating, and other characteristics of the acoustic waves transmitted therein. For other bodies under test with broadband sources, dispersive wave propagation, or source origination from unknown locations, such that they that do not lend themselves to conventional time reversal techniques, these bodies may use the techniques herein for real time analysis of signals based on their ability to determine the proper timing differentials without fitting a closed form set of timing differentials to each event detected.

The composite materials in a composite test vessel provide a viscoelastic media in which the transient elastic waves are measured. The polymer matrix in a composite material may be comprised of a viscoelastic resin such that attenuation increases with frequency. An exemplary composite material can attenuate higher frequencies many times more than lower frequencies. Some analyses of these bodies may require review of frequencies in the body, and as used herein, the term "frequency under test" or "frequency of interest" means a frequency for which analyses are required or used for the specific analyses being performed (e.g., to properly identify a damage mechanism originating from within the microstructure, or to identify a location of an event in the body).

In addition, each of these transient elastic waves may have a separate speed of travel through the medium, caused by dispersion of the transient elastic waves representing an event, and creating additional need for maintaining a positive overlap. Therefore, for design purposes of the array of transducers, the frequencies of interest will be analyzed for a "slowest moving wave component" of the frequency of interest which is used to designate herein the portion of the transient elastic waves with the slowest velocity in the subject material. As described further herein, the slowest moving wave may be used to determine several of the required parameters of the arrays of transducers and required computational power of the time-shifting hardware using the methods herein.

In addition, in the presence of material anisotropy the slowest velocities may be different in different directions. Therefore, the array configurations must consider the characteristics of incident waves and the need for capturing the entirety of an event possibly in boundary sample sets processed with both surrounding sets of samples.

As further described herein, the acceptable overlap of processing times and samples may be controlled during operation of the systems and methods herein to adjust operation and detection of events in the body under test. For example, while processing times may fluctuate between events, an additional process monitoring the desired and actual overlaps available and used for each detected event may be employed to monitor the methods herein.

FIGS. 4 and 5 show the effects of alternate orientations of a transient vibration source with respect to a transducer array. The transient vibration source (e.g., an event, material facture, etc.) induces transient elastic waves in the body under test. This source will produce a broad spectrum of vibration frequencies that may each have a transmission speed based on the elastic medium and geometry. The methods herein adapt an array of transducers measuring the body under test such that the slowest moving wave propagating from the source will be detected by each of the elements at least within the overlap time or related sample overlap available during processing.

The methods described herein provide for processing in real time sets of data from signals with overlap between the sets of data consisting of a maximum time difference between the event arriving and completing at each of the transducer elements in the array. In one embodiment, the array configuration and processing is adapted such that events from any location in the body under test may be captured by the array with a positive overlap regardless of angle of propagation, capturing the slowest moving waves and allowing combination of an entire event even if from a source angle that maximizes detection delay between the elements in the array (e.g., aligned parallel with the axis of a 1D array).

In some embodiments, more overlap is available due to computational processing efficiencies than is required by the physical array configuration, the slowest moving transient elastic wave component, and the temporal extent of relevant events. In alternate embodiments, the array configuration and processing are adapted to adjust the overlap between angles from zero overlap to a positive overlap.

As shown in FIG. 4, a source of transient elastic waves emanating from an angle perpendicular to a linear (1D) array (i.e., at an angle of 90 degrees) will deliver the transient elastic waves to the transducer array with a minimum of delay between the elements. For example, if the source or event is far enough away from the transducer array, a planar assumption may be made for the waves and the arrival time difference between transducer array elements will be near zero.

Alternatively, as shown in FIG. 5, a source of transient elastic waves emanating from an angle that is in line with a linear (1D) transducer array (i.e., at zero degrees, parallel to an axis of the array) will have a maximum delay time between transducer signals for the array. For example, the source waves incident on the first element will need to be delay-matched with each successive element in the array by an integer number of delays based on the position of the transducer producing the respective signal. As described further herein, other angles may create delays which require different delay times to bring the signals into time coherency. These different angles may create different SNR increases in the combined signal based on the combining efficiencies and the described methods' ability to correlate and cancel the noise as described herein.

Figure 6:
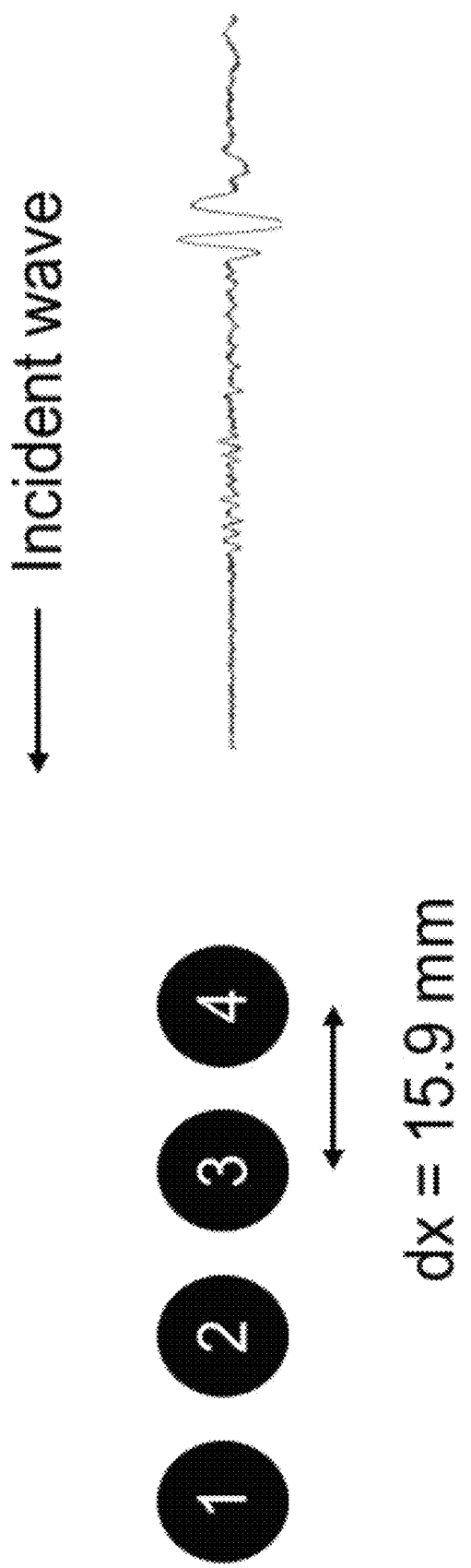
FIG. 6 shows details of an exemplary transient elastic wave as measured by individual elements from a source at a parallel angle of incidence.

FIG. 6 shows details of an exemplary transient elastic vibration wave as measured by individual elements from a source at an angle of zero degrees (i.e., wave propagation in a parallel direction to the array). An incident wave with particular speed based upon the dispersion relations, and coming from a direction in line (i.e., parallel) with an axis of the transducer array. This direction maximizes the time differential between signals received by each transducer, while other masking distortions will also be present between the received transient elastic waves (e.g., due to dispersion, attenuation, electronic noise). As described further herein, time differentials between the signals received may be determined in real time to combine signals into coherence with a designated element in the array (e.g., element 2, element 3), thus increasing the effective SNR in real time and allowing enhanced processing steps (e.g., normalizing, storing decision in real time). By bringing each of the signals into coherence with a central element of the array, such as element 2 or element 3 in the linear (1D) 4 element linear array, the processing requirements may be reduced by creating smaller adjustments to each signal. The following figures include measured signals from linear (1D) arrays of four elements, including the summed signals as produced in real time ensuring the methods described herein.

Figure 7:
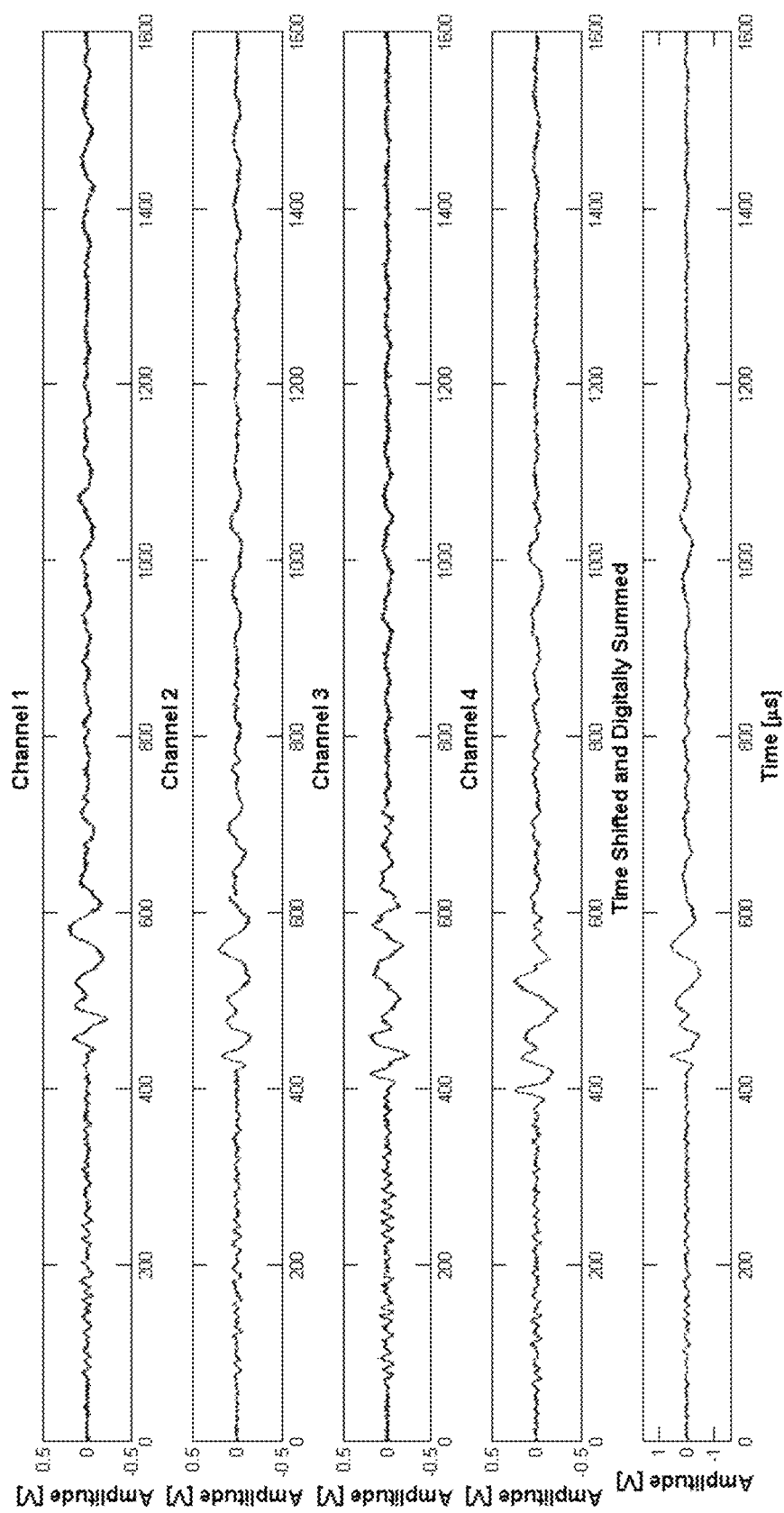
FIG. 7 shows signals detected from a parallelly oriented pencil-lead-break source to an array of transducers, along with a digitally summed and shifted signal as described herein.

FIG. 7 shows signals detected from a pencil lead break source at 0 relative degrees to an array of transducers, along with a digitally summed and shifted signal as described herein. In this embodiment, the source location is the same as shown in the prior figure, emphasizing the time differential between the signals. As shown the induced event (i.e., a pencil lead break) creates waves that are first detected on Channel 4, then Channels 3-1 in sequential reverse order. As described further herein, the combination of the signals (e.g., time shifted and summed signal), shown in the fifth trace at the bottom, shows a combined signal with a greater amplitude than each of the constituent signals. In another embodiment, the summation of the signals may be scaled, normalized, or otherwise modified to create a better combined signal.

As shown in the combined signal, the signal to noise ratio for the individual signals is reduced via the processes herein (i.e., correlation, time differential calculations, combination), and this SNR gain for the combined signal is detailed in later figures. The SNR gains are dependent on the angle of the incidence of the waves from the source on the array, the body under test (e.g., its dispersive and other characteristics), and the frequency content of the transient elastic waves from the source, but are shown achievable and robust using the methods described herein.

In one embodiment, the timing differential calculations for combination are created by determining the maximum of the cross correlation product between the signal from a predetermined reference element (e.g., element 2) and the signals from each of the other individual elements. However, there are other time shifting algorithms and/or calculations that may be adapted for use within the present real time environment that may create acceptably accurate timing differentials to complete the processes described herein. Therefore, one or more of the several existing algorithms and/or calculations may be adapted to create the combined signals used by the methods and systems described herein.

Cross-correlation is a mathematical construct which provides a measure of the similarity of two time-series as a function of the lag in sample points of one signal relative to the other. The below equation provides the mathematical definition of the $m^{th}$ cross-correlation coefficient for two signals x and y, each of which has length N.

$$\hat{R}_{xy}(m) = \begin{matrix} \sum_{n=0}^{N-m-1} x_{n+m} \cdot y_n & m \geq 0 \\ \hat{R}_{yx}(-m) & m < 0 \end{matrix}$$

By time shifting the two series through a number of lags, the amount of shift between the two series may be determined by the point at which the two signals are most similar or when the waveforms exhibit maximum coherency (i.e., $\hat{R}_{xy}$ is maximum). From a conceptual view point, FIGS. 4 and 5 shows how each of the four individual elements of the phased array will receive the wave fields at slightly offset times from one another as the stress waves propagate through the medium. Through the use of cross-correlation, the waveforms captured by all four elements in the array can be shifted to appear as if they were all detected simultaneously. As an example of determining an upper limit on the number of computations that would be required for a given array, the worst case relative to the amount of inter-element time difference (i.e., parallel wave incidence) is considered, FIG. 6. From inspection of FIG. 6, it is seen that the wave field will incident element 4 first, and element 1 last. Assuming the slowest moving component of the flexure mode (i.e., lowest frequency of interest) for most engineering materials has a velocity of no more than 0.5 mm/μs in most practical MAE inspection scenarios, an equation to establish the largest amount of time (or lags) needed to shift waveforms into register may be written as $$t = \frac{n \cdot dx}{c_f} = \frac{n \cdot 15.9 \text{ mm}}{0.5 \text{ mm}/\mu s}$$

where n equals the number of elements to shift, dx is the inter-element spacing or pitch, and $c_f$ is the slowest moving flexure mode velocity. In this example and orientation, shifting all waveforms to elements 2 require n=2 (t=63.6 μs or 318 lags if sampled at 5 MS/s), whereas shifting to elements 1 or 4 would require n=3 (t=95.4 μs or 477 lags if sampled at 5 MS/s). Therefore, to minimize the number of required computations and without loss of generality, all waveforms were shifted to element 2 which will henceforth be referred to as the reference element. While the computational requirements of the time shifting algorithm may be reduced by selecting an advantageous reference element, the maximum width (or length depending upon orientation) of number of elements of the array to cover must be considered when determining the sample overlap requirements.

Figure 8:
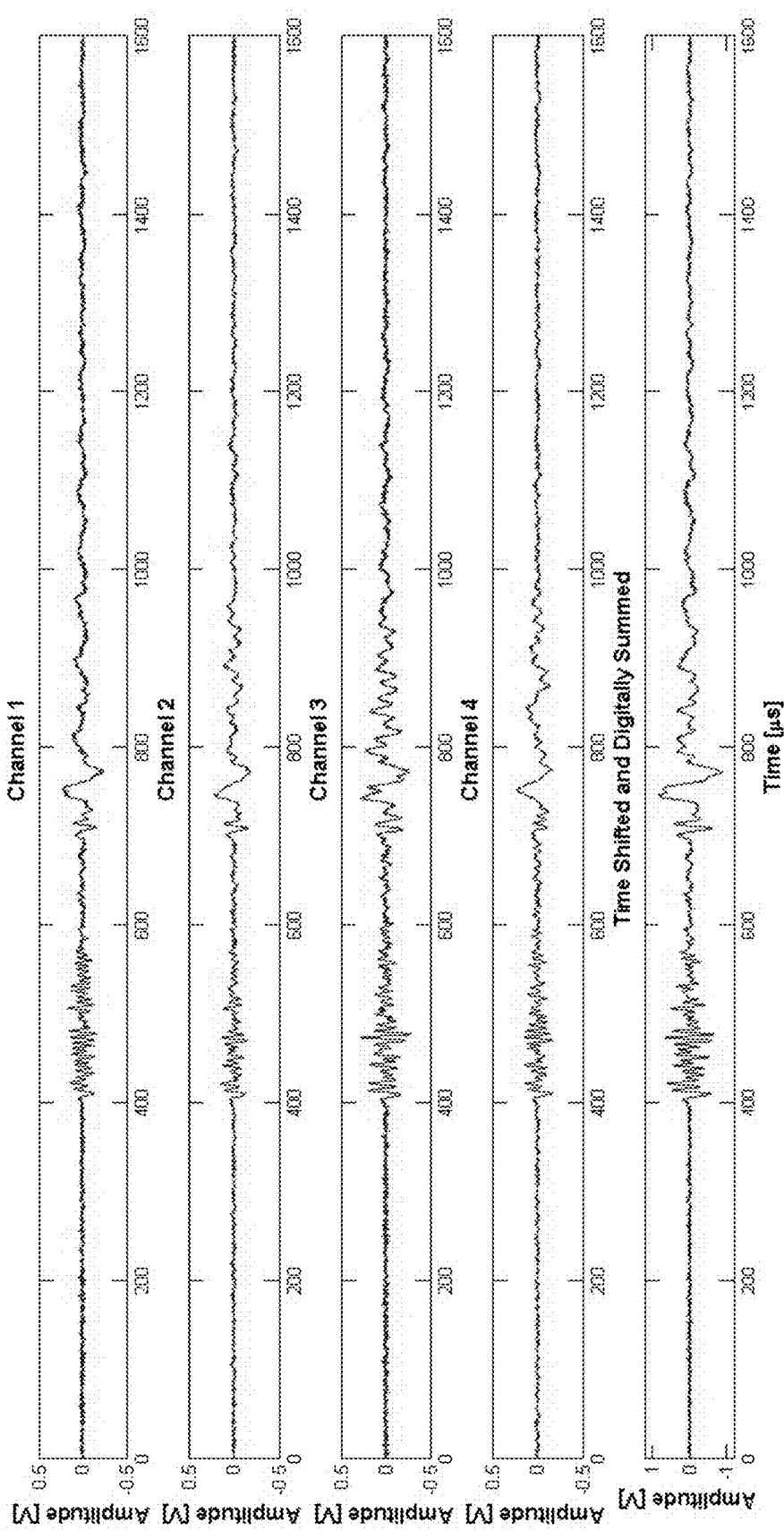
FIG. 8 shows signals detected from a perpendicularly oriented pencil-lead-break source to an array of transducers, along with a digitally summed and shifted signal as described herein.

FIG. 8 shows signals detected from a pencil lead break source at 90 relative degrees to an array of transducers, along with a digitally time shifted and summed signal as described herein. In this embodiment, the source is located at 90 degrees to an axis of the array, thus allowing the transient elastic waves to reach each of the transducers nearly simultaneously. However, the methods described herein may still be used to increase SNR as shown in the combined signal trace.

As in other embodiments, this embodiment may use the same time differential calculations and processing techniques as described for use with any other event emitting transient elastic waves from any source location. To be clear, a system and methods described herein will not know, in most embodiments, anything about a source location of the waves, and thus the same determinations and calculations will be necessary for each set of samples received. In other embodiments, some information is known about the source location and adaptations may be made to the methods and systems herein based on this information. Therefore, the amplifications and triggering decisions for each channel must account for variations in received waves from different angles.

FIG. 9 shows timing differential calculated for various angles of incidence for summation of signals in an exemplary linear array of four elements. As anticipated, for a source with perpendicular (90°) orientation, the time shift between elements is relatively low and is steadily increasing as source orientation nears a parallel (0°) source location.

Also, the timing differentials shown in the figure are all determined with the reference element being an interior element (element 2) of the linear array. In several embodiments, the timing differentials are calculated for an interior element of the array, minimizing timing differentials and the requirements on processing power between sample sets. Furthermore, the required timing differentials for summing the signals may be different for a particular element based on the material or body under test and calculating those differentials in real time after receiving signals from the event allows for minute but important changes in the timing differentials to be made in order to optimize the real time detection and SNR-increasing aspects of the systems and methods herein.

FIG. 10 shows increases in flexure mode peak amplitude for alternative summation possibilities for a body under test as compared to the methods described for digital real time summation herein. Each row of the figure provides results comparing direct analog versus digital time shifting followed by summation from different angles of propagation. The reported summation gains that are available via analog summation provide for modest SNR gains over a single channel, however, they do not increase SNR sensitivity by as much or as consistently as the disclosed digitally shifted and summed signal. The disclosed combined signals provide the SNR gains reported in the phased array modal acoustic emission (PA-MAE) systems.

Increases in SNR are important for the methods and systems described herein, but the consistency of SNR increases is also an important factor in system design for the goal of providing full coverage of a body under test while minimizing the number of arrays that must be placed on the structure. By increasing the SNR, the number of required transducer arrays can be reduced by increasing the effective dynamic range of the system.

Therefore, the real time processing requirements must be met to prepare a triggering scheme. the analog summation techniques shown cannot provide the benefits of the methods and systems herein because they both provide a lesser gain in SNR and provide a varying SNR gain depending on the angle of propagation. Because the systems and methods herein are used with arrays to detect waves at any angle of propagation, variance in the SNR increase can further complicate the process of triggering events being detected.

Thus, the methods and systems described herein must be adapted to measure the transient elastic waves to provide the proper SNR boosts across many or all angles of propagation. The methods and systems allow receiving signals with increased SNR from an unknown source location in the material under test with dispersive characteristics, while still allowing the system to operate in real time.

In some embodiments, arrays using the systems and methods herein may be able to create these SNR gains covering many angles of source location, allowing a smaller array to monitor a larger body under test. For example, a pressure vessel may be held within a transportation container and an array may be attached only to a portion that is accessible, yet it will still be able to apply those SNR gains to sensing events originating in other portions of the pressure vessel. By accounting for the dispersive characteristics in the material under test, the methods herein allow an array with designed pitch to process in real time the transient elastic waves originating from any location on the material body under test, including while a portion of the body under test not being accessible. For example, these methods and systems may be used to necessitate a smaller number of sensor arrays and/or arrays that can be used on materials under test without physical access to a portion of the body of material.

This patent description and drawings are illustrative and are not to be construed as limiting. It is clear that many modifications and variations of this embodiment can be made by one skilled in the art without departing from the spirit of the novel art of this disclosure. While specific parameters, device configurations, parameters of components, and thresholds may have been disclosed, other reference points can also be used. These modifications and variations do not depart from the broader spirit and scope of the present disclosure, and the examples cited here are illustrative rather than limiting.

What is claimed is:

1. A system comprising:
    a multi-element transducer array for attaching to a body of material under test that is configured to transmit a plurality of broadband signals representing propagating transient elastic broadband vibrations in the body of material under test and containing frequencies in a frequency band of interest of the transient elastic broadband vibrations, the frequency band of interest including a slowest-moving wave component of the transient elastic broadband vibrations;
    wherein the multi-element transducer array is configured with a maximum distance between furthest elements of the multi-element transducer array that is sufficiently small to capture a transit of a wave of the slowest-moving wave component of the transient elastic broadband vibrations within a transit time-window;
    wherein the transit time-window is less than a positive processing overlap time that includes times of the broadband signals that are able to be processed in real time by the system both with a first time-window and with a second time-window that immediately follows the first time-window of the broadband signals;
    a receiver circuit configured to process a plurality of broadband signals received from the multi-element transducer array, the receiver circuit further comprising:

a time-coherency circuit configured to determine a plurality of time delays between a first reference broadband signal of the plurality of broadband signals and the other broadband signal(s) of the plurality of broadband signals such that when the plurality of broadband signals are time-shifted respectively by the plurality of time delays, a plurality of time-shifted broadband signals are created that are in time-coherence with each other;

a combination circuit configured to create a combined broadband signal based on a summation of the plurality of time shifted broadband signals; and a threshold-determining circuit configured to determine which values of the combined broadband signal should be stored based on the values of the combined broadband signal being above a threshold at a time when none of the plurality of the time shifted broadband signals have a value over the threshold; and a combined broadband signal non-transitory memory and signal determined to be stored in the combined broadband signal non-transitory memory by the threshold-determining circuit.

2. The system of claim 1, further comprising:

a fluid filled compliant bladder configured for connection between the body of material under test and the multi-element transducer array and configured for coupling the slowest moving wave component transmitted through the body of material under test to the multi-element transducer array.

3. The system of claim 1, further comprising:

a threshold response circuit in communication with the time coherency circuit for capturing a time of an event in one broadband signal of the plurality of broadband signals that surpasses a threshold.

4. The system of claim 1, wherein the transit time window is represented by a transit number of samples;

wherein the positive processing overlap time is represented by a positive overlap of samples;

wherein the transit number of samples is less than the positive overlap of samples; and wherein the positive overlap of samples includes one or more samples of the broadband signals that are able to be processed in real time by the system both with a first window of samples of a plurality of processed samples representing the transient elastic broadband vibrations and with a second window of samples of the plurality of processed samples that immediately follows the first window of samples in the plurality of processed samples of the broadband signals.

5. The system of claim 1, wherein the time coherency circuit is configured to compute the plurality of time delays between the first reference broadband signal of the plurality of broadband signals and the other broadband signal(s) of the plurality of broadband signals based upon a plurality of cross correlation coefficients computed between the first reference broadband signal and the other broadband signal(s) of the plurality of broadband signals.

6. The system of claim 2, wherein the fluid filled compliant bladder is configured to acoustically couple a rough surface of the body of material under test to a transducer of the multi-element transducer array.

* * * * *